United States Patent
Streeter

(10) Patent No.: US 7,316,922 B2
(45) Date of Patent: Jan. 8, 2008

(54) METHOD FOR PRESERVING ORGANS FOR TRANSPLANT

(75) Inventor: Jackson Streeter, Reno, NV (US)

(73) Assignee: Photothera Inc., San Diego, CA (US)

( * ) Notice: Subject to any disclaimer, the term of this patent is extended or adjusted under 35 U.S.C. 154(b) by 459 days.

(21) Appl. No.: 10/338,949

(22) Filed: Jan. 8, 2003

(65) Prior Publication Data

US 2004/0014199 A1    Jan. 22, 2004

Related U.S. Application Data

(60) Provisional application No. 60/353,639, filed on Jan. 31, 2002, provisional application No. 60/347,171, filed on Jan. 9, 2002.

(51) Int. Cl.
*A01N 1/02* (2006.01)
(52) U.S. Cl. .............. 435/284.1; 435/307.1; 250/455.11; 362/101; 362/154
(58) Field of Classification Search ......... 435/173.8, 435/292.1, 284.1; 362/154
See application file for complete search history.

(56) References Cited

U.S. PATENT DOCUMENTS

| | | | |
|---|---|---|---|
| 3,735,755 A | 5/1973 | Eggleton et al. |
| 3,810,367 A | 5/1974 | Peterson |
| 4,315,514 A | 2/1982 | Drewes et al. |
| 4,343,301 A | 8/1982 | Indech |
| 4,630,273 A | 12/1986 | Inoue et al. |
| 4,633,872 A | 1/1987 | Chaffee et al. |
| 4,669,466 A | 6/1987 | L'Esperance |
| 4,798,215 A | 1/1989 | Turner |
| 4,846,196 A | 7/1989 | Wiksell et al. |
| 4,930,504 A | 6/1990 | Diamantopolous et al. |
| 4,951,482 A | 8/1990 | Gilbert |
| 4,951,653 A | 8/1990 | Fry et al. |
| 4,966,144 A | 10/1990 | Rochkind et al. |
| 5,029,581 A | 7/1991 | Kaga et al. |
| 5,037,374 A | 8/1991 | Carol |
| 5,054,470 A | 10/1991 | Fry et al. |
| 5,150,704 A | 9/1992 | Tatebayashi et al. |

(Continued)

FOREIGN PATENT DOCUMENTS

DE      3200584 A1    7/1983

(Continued)

OTHER PUBLICATIONS

U.S. Appl. No. 10/682,379, filed Oct. 9, 2003, De Taboada et al.

(Continued)

*Primary Examiner*—William H. Beisner
(74) *Attorney, Agent, or Firm*—Knobbe Martens Olson & Bear LLP

(57) ABSTRACT

Methods and apparatus for preserving tissue such as harvested organs for transplant are described. A preferred method includes delivering to a harvested organ an effective amount of electromagnetic energy, the electromagnetic energy having a wavelength in the visible to near-infrared wavelength range, wherein delivering the effective amount of electromagnetic energy includes selecting a predetermined power density (mW/cm$^2$) of electromagnetic energy to deliver to the organ while in hypothermic or normothermic storage. A preferred apparatus includes a container having a cooling chamber to receive the harvested organ and at least one light source mounted on the container to illuminate the interior cooling chamber, said light source emiting light which produces a biostimulative effect on tissue placed in the cooling chamber thereby preventing or retarding damage to the tissue during storage or transport.

23 Claims, 1 Drawing Sheet

U.S. PATENT DOCUMENTS

| | | | |
|---|---|---|---|
| 5,259,380 A | 11/1993 | Mendes et al. | |
| 5,267,294 A | 11/1993 | Kuroda et al. | |
| 5,282,797 A | 2/1994 | Chess | |
| 5,358,503 A | 10/1994 | Bertwell et al. | |
| 5,401,270 A | 3/1995 | Muller et al. | |
| 5,441,495 A | 8/1995 | Liboff et al. | |
| 5,445,146 A | 8/1995 | Bellinger | |
| 5,445,608 A | 8/1995 | Chen et al. | |
| 5,464,436 A | 11/1995 | Smith | |
| 5,501,655 A | 3/1996 | Rolt et al. | |
| 5,511,563 A | 4/1996 | Diamond | |
| 5,540,737 A | 7/1996 | Fenn | |
| 5,580,550 A | 12/1996 | Gough et al. | |
| 5,580,555 A | 12/1996 | Schwartz | |
| 5,601,526 A | 2/1997 | Chapelon et al. | |
| 5,616,140 A | 4/1997 | Prescott | |
| 5,621,091 A | 4/1997 | Kunkel et al. | |
| 5,622,168 A | 4/1997 | Keusch et al. | |
| 5,627,870 A | 5/1997 | Kopecky | |
| 5,640,978 A | 6/1997 | Wong | |
| 5,643,334 A | 7/1997 | Eckhouse et al. | |
| 5,728,090 A | 3/1998 | Martin et al. | |
| 5,755,752 A | 5/1998 | Segal | |
| 5,762,867 A * | 6/1998 | D'Silva | 422/44 |
| 5,817,008 A | 10/1998 | Rafert et al. | |
| 5,842,477 A | 12/1998 | Naughton et al. | |
| 5,843,073 A | 12/1998 | Sinofsky | |
| 5,849,585 A | 12/1998 | Mather et al. | |
| 5,879,376 A | 3/1999 | Miller | |
| 5,902,741 A | 5/1999 | Purchio et al. | |
| 5,928,207 A | 7/1999 | Pisano et al. | |
| 5,928,945 A | 7/1999 | Seliktar et al. | |
| 5,954,762 A | 9/1999 | Di Mino et al. | |
| 5,983,141 A | 11/1999 | Sluijter et al. | |
| 5,989,245 A | 11/1999 | Prescott | |
| 6,033,431 A | 3/2000 | Segal | |
| 6,042,531 A | 3/2000 | Holcomb | |
| 6,045,575 A | 4/2000 | Rosen et al. | |
| 6,046,046 A | 4/2000 | Hassanein | |
| 6,060,306 A | 5/2000 | Flatt et al. | |
| 6,063,108 A | 5/2000 | Salansky et al. | |
| 6,107,325 A | 8/2000 | Chan et al. | |
| 6,107,608 A | 8/2000 | Hayes | |
| 6,112,110 A | 8/2000 | Wilk | |
| 6,117,128 A | 9/2000 | Gregory | |
| 6,129,748 A | 10/2000 | Kamei | |
| 6,143,878 A | 11/2000 | Koopman et al. | |
| 6,146,410 A | 11/2000 | Nagypal et al. | |
| 6,149,679 A | 11/2000 | Di Mino et al. | |
| 6,156,028 A | 12/2000 | Prescott | |
| 6,179,771 B1 | 1/2001 | Mueller | |
| 6,187,210 B1 | 2/2001 | Lebouitz et al. | |
| 6,198,958 B1 | 3/2001 | Ives et al. | |
| 6,210,317 B1 | 4/2001 | Bonlie | |
| 6,214,035 B1 | 4/2001 | Streeter | |
| 6,221,095 B1 | 4/2001 | Van Zuylen et al. | |
| 6,267,780 B1 | 7/2001 | Streeter | |
| 6,273,905 B1 | 8/2001 | Streeter | |
| 6,277,974 B1 | 8/2001 | Lo et al. | |
| 6,290,713 B1 | 9/2001 | Russell | |
| 6,290,714 B1 | 9/2001 | Streeter | |
| 6,312,451 B1 | 11/2001 | Streeter | |
| 6,344,050 B1 | 2/2002 | Chen | |
| 6,358,272 B1 | 3/2002 | Wilden | |
| 6,363,285 B1 | 3/2002 | Wey | |
| 6,364,907 B1 | 4/2002 | Obochi et al. | |
| 6,379,295 B1 | 4/2002 | Woo | |
| 6,395,016 B1 | 5/2002 | Oron et al. | |
| 6,397,107 B1 | 5/2002 | Lee et al. | |
| 6,402,678 B1 | 6/2002 | Fischell et al. | |
| 6,421,562 B1 | 7/2002 | Ross | |
| 6,443,974 B1 | 9/2002 | Oron et al. | |
| 6,443,978 B1 | 9/2002 | Zharov | |
| 6,471,716 B1 | 10/2002 | Pecukonis | |
| 6,514,220 B2 | 2/2003 | Melton, Jr. et al. | |
| 6,537,304 B1 | 3/2003 | Oron | |
| 6,551,308 B1 | 4/2003 | Muller et al. | |
| 6,663,659 B2 | 12/2003 | McDaniel | |
| 2001/0044623 A1 | 11/2001 | Chen | |
| 2002/0068927 A1 | 6/2002 | Prescott | |
| 2002/0087205 A1 | 7/2002 | Chen | |
| 2002/0123781 A1 | 9/2002 | Shanks et al. | |
| 2002/0188334 A1 | 12/2002 | Carlgren | |
| 2002/0198575 A1 | 12/2002 | Sullivan | |
| 2003/0125782 A1 | 7/2003 | Streeter | |
| 2003/0144712 A1 | 7/2003 | Streeter | |
| 2003/0167080 A1 | 9/2003 | Hart et al. | |
| 2003/0212442 A1 | 11/2003 | Streeter | |
| 2003/0216797 A1 | 11/2003 | Oron | |
| 2004/0014199 A1 | 1/2004 | Streeter | |
| 2004/0044384 A1 | 3/2004 | Leber et al. | |
| 2004/0132002 A1 | 7/2004 | Streeter | |
| 2004/0220513 A1 | 11/2004 | Streeter | |
| 2004/0260367 A1 | 12/2004 | De Taboada et al. | |
| 2005/0009161 A1 | 1/2005 | Streeter | |
| 2005/0107851 A1 | 5/2005 | De Taboada et al. | |

FOREIGN PATENT DOCUMENTS

| | | |
|---|---|---|
| DE | 41 08 328 A1 | 9/1992 |
| DE | 42 13 053 A1 | 10/1993 |
| DE | 295 15 096 U1 | 1/1996 |
| EP | 0 130 950 | 11/1990 |
| EP | 0 763 371 A2 | 3/1997 |
| EP | 0 783 904 A2 | 7/1997 |
| EP | 1 226 787 A2 | 7/2002 |
| JP | 04023634 | 2/1992 |
| WO | WO 96/36396 | 11/1996 |
| WO | WO 98/04321 | 2/1998 |
| WO | WO 98/22573 | 5/1998 |
| WO | WO 99/42178 | 8/1999 |
| WO | WO 99/62599 A1 | 12/1999 |
| WO | WO 00/035534 A1 | 6/2000 |
| WO | WO 05/025672 A1 | 3/2005 |

OTHER PUBLICATIONS

U.S. Appl. No. 10/448,262, filed May 29, 2003, Oron et al.
U.S. Appl. No. 10/612,709, filed Jul. 2, 2003, Streeter.
U.S. Appl. No. 10/723,171, filed Nov. 26, 2003, Streeter.
U.S. Appl. No. 10/764,986, filed Jan. 6, 2004, Streeter.
PCT/US03/00747, filed Sep. 1, 2003, International Search Report.
PCT/US02/36808, filed Nov. 15, 2002, International Search Report.
PCT/CA99/00156, filed Feb. 23, 1999, International Search Report.
PCT/US04/029724, filed Sep. 10, 2004, International Search Report.
PCT/US2005/004873, filed Feb. 11, 2005, Photothera, Inc.
*Optical Properties of Tissues with Strong (Multiple) Scattering*, source unknown.
Van Brugel, Hans H.F.I., et al., *Power Density and Exposure Time of He-Ne Laster Irradiation ar eMore Important than Total Energy Dose in Photo-Biomoducation of Human Fibroblasts* In Vitro, 1992, Wiley-Liss, Inc.
Agov, B.S., et al., *On the mechanism of therapeutic action of helium-neon laser in ischemic heart disease*, KLIN MED (Mosc), 1985, pp. 102-105 (Abstract only).
Arvidsson, Andreas, et al., *Neuronal replacement from endogenous precursors in the adult rat brain after stroke*, Nature Medicine, vol. 8, No. 9, Sep. 2002, pp. 963-970.
Brazzle, John, et al., *Active Microneedles with Integrated Functionality*, Technical Digest of the 2000 Solid-State Sensor and Actuator Workshop, Department of Bioengineering, University of Utah, Salt Lake City, Utah 84112 (five pages).

Brill, G.E., et al., *Modifying influence of low level laser irradiation on the relationships in endothelial cell—blood platelet system*, 10th Congress of the European Society for Photobiology, Vienna, Austria (one page).

Byrnes, K.R., et al., *Light Therapy Promotes Axonal Regeneration After Acute Spinal Cord Injury in Adult Rats*, Program No. 275.2, Society for Neuroscience, 2003, Abstract.

Cohen, Michael A., *Method of Forming Microneedles and other Micron-Scale Transdermal Probes*, Office of Technology Licensing, University of California, Berkeley, http://otl.berkeley.edu/technology/inventiondetail.php/1000335, Abstract (two pages).

Dirnagl, Ulrich, et al., *Pathobiology of ischaemic stroke: an integrated view*, TINS, vol. 22, No. 9, 1999, pp. 391-397.

Eells, J.T., et al., *Therapeutic photobiomodulation for methanol-induced retinal toxicity*, Proceedings National Academy of Science (PNAS), vol. 100, No. 6, Mar. 18, 2003, pp. 3439-3444.

Elimadi, Aziz, et al., *Trimetazidine Counteracts the Hepatic Injury Associated with Ischemia-Reperfusion by Preserving Michondrial Function*, Journal of Pharmacology and Experimental Therapeutics, vol. 286, No. 1, 1998, pp. 23-28.

Gage, Fred H., *Brain, Repair Yourself*, Scientific American, Sep. 2003, pp. 47-53.

Gasparyan, Levon V., et al., *Low Level Laser Therapy of Male Genital Tract Chronic Inflammations*, WALT 2-nd Congress (Kansas City, USA), 1998 (two pages).

Gasparyan, L.V., et al., *The influence of LED irradiation at different wavelengths on functional activity of blood platelets*, 10th Congress of the European Society for Photobiology, Vienna, Austria, 2003 (one page).

Gasparyan, L.V., et al., *The influence of LED irradiation at different wavelengths with antioxidants on functional activity of blood platelets*, Laser, Florence, 2003 (one page).

Gasparyan, Levon V., *Biochemical and Biophysical Effects of Low Level Laser Irradiation*, MAL 2000, Helsinki, Finland (three pages).

Gasparyan, Levon V., *Experience of Russian (former USSR) Scientists in LLLT and UV Blood Irradiation*, MAL 2000, Helsinki, Finland (four pages).

Gasparyan, Levon V., *Investigation of Sensations, Associated with Laser Blood Irradiation*, WALT 2-nd Congress (Kansas City, USA), 1998 (two pages).

Gasparyan, Levon V., *Millimeter Wave Therapy*, MAL 2000, Helsinki, Finland (three pages).

Gross, Garrett J., et al., *Mechanisms of Postischemic Contractile Dysfunction*, Myocardial Protection From Surgical Ischemic-Reperfusion Injury, An International Symposium, Asheville, North Carolina, Sep. 21-24, 1997, pp. 1898-1904.

Hammon, John W. Jr, MD, et al., *Myocardial Protection Form Surgical Ischemic-Reperfusion Injury*, Ann Thorac Surg 1999:68:1897.

Iadecola, Costantino, et al., *Inhibition of inducible nitric oxide synthase ameliorates ischemic damage*, Am. J. Physiol., vol. 268, 1995, pp. R286-R292.

Karu, Tiina, *Mechanisms of Low-Power Laser Light Action on Cellular Level, Effects of Low-Power Light on Biological Systems V*, Proceedings of SPIE, Jul. 7, 2000, vol. 4159, 2000.

Karu, T.I., *Low power laser therapy*, in Biomedical Photonics Handbook, Ch. 48, Editor-in-Chief Tuan Vo-Dinh, Boca Raton, CRC Press, 2003.

Karu, Tiina, *Mechanisms of interaction of monochromatic visible light with cells*, Proc. SPIE, vol. 2630, pp. 2-9.

Karu, Tiina, *Photobiological Fundamentals of Low Power Laser Therapy*, IEEE Journal of Quantum Electronics, vol. QE-23, No. 10, Oct. 1987, pp. 1703-1717.

*The Laser Exchange: Delivering the medicine of the future*, www.laserexchange.co.uk/laser-therapy/ultrasoun.htm, 42 pages.

Leung, Mason C.P., et al., *Treatment of Experimentally Induced Transient Cerebral Ischemia with Low Energy Laser Inhibits Nitric Oxide Synthase Activity and Up-Regulates the Expression of Transforming Growth Factor-Beta I*, Lasers in Surgery and Medicine, vol. 31, 2002, pp. 283-288.

Minoru, Asahi, et al, *Expression of Interleukin-1 [beta] Converting Enzyme Geme Family and bcl-2 Gene Family in the Rat Brain Following Permanent Occlusion of the Middle Cerebral Artery*, Journal of Cerebral Blood Flow & Metabolism, vol. 17(1), Jan. 1997, pp. 11-18.

Mochizuki-Oda, Noriko, et al., *Effects of near-infra-red laser irradiation on adenosine triphosphate and adenosine diphosphate contents of rat brain tissue*, Neuroscience Letters 323, May 3, 2002, pp. 207-210.

Nishioka, Norman S., et al., *Reflection and Transmission of Laser Light From the Esophagus: The Influence of Incident Angle*, Gastroenterology, vol. 94, 1988, pp. 1180-1185.

Olesin, Al, et al., *Laser irradiation of venous blood for production of reperfusion syndrome in myocardial infarction*, Patologisheskaia fiziologiia, 1992 (Abstract only).

Oron, Uri, et al., *Attenuation of Infarct Size in Rats and Dogs after Myocardial Infarction by Low-Energy Laser Irradiation*, Lasers in Surgery and Medicine, vol. 28, 2001, pp. 204-211.

Oron, Uri et al., *Low-Energy Laser Irradiation Reduces Formation of Scar Tissue After Myocardial Infarction in Rats and Dogs*, Circulation, vol. 103, Jan. 16, 2001, pp. 296-301.

Park, James L., Ph.D., et al., *Mechanisms of Myocardial Reperfusion Injury*, The Annals of Thoracic Surgery, Official Journal of The Society of Thoracic Surgeons and the Southern Thoracic Surgical Association, vol. 68, No. 5, Nov. 1999, pp. 1905-1912.

Semenza, Gregg L., et al., *Regulation of Mammalian O; Homeostasis by Hypoxia-Inducible Factor I*, Ann. Rev. Cell Dev. Biol., vol. 15, 1999, pp. 551-578.

Stys, Peter K., *Anoxis and Ischemic Injury of Myelinated Axons in CNS White Matter: From Mechanistic Concepts to Therapeutics*, J. Cereb. Blood Flow Metab., vol. 18, No. 1, Jan. 1998, pp. 2-25.

*Is LLLT Different from Ultrasound?*, http://www.thorlaser.com/LLLT/is-LLLT-diff-from-ultrasound.htm, 2 pages.

Product List, Tho, lllt, LLLT, *Low Level Laser Therapy, Laz.*, http://www.thorlaser.com/prodlist/index.html, Oct. 6, 1999, pp. 1-4.

Specifications, Thor, lllt, LLLT, *Low Level Laser Therapy, low level laser therapy*, http://www.thorlaser.com/specs, Oct. 6, 1999, pp. 1-2.

100mW, Thor, lllt, LLLT, *Low Level Laser Therapy, low level laser therapy, Lazer, Thorl.*, http://www.thorlaser.com/_specs/_100mW.html, Oct. 6, 1999, p. 1.

200mW, Thor, lllt, LLLT, *Low Level Laser Therapy, low level laser therapy, Lazer, Thorl.*, http://www.thorlaser.com/_specs/200m_W.html, Oct. 6, 1999, p. 1.

500mW, Thor. lllt, LLLT, *Low Level Laser Therapy, low level laser therapy, Lazer, Thorl.*, http://www.thorlaser.com/_specs/500m_W.html, Oct. 6, 1999, p. 1.

200mW, Thor, lllt, LLLT, *Low Level Laser Therapy, low level laser therapy, Laser, Thorl.*, http://www.thorlaser.com/_specs/200m_W650nm.html, Oct. 6, 1999, p. 1.

680nm PROBE, Thor, lllt, LLLT, *Low Level Laser Therapy, low level laser therapy, Laser*, http://www.thorlaser.com/_specs/680.html, Oct. 6, 1999, p. 1.

Toon, John, *Taking the "Ouch" Out of Needles: Arrays of Micron-Scale "Microneedles" Offer New Technique for Drug Delivery*, Georgia Tech Research News, Jun. 22, 1999 (three pages).

Toricelli, P., et al., *Laser Biostimulation of cartilage: in vitro evaluation*, Biomed Pharmacother 2001, vol. 55, pp. 117-120.

Tuchin, Valery, *Tissue Optics: Light Scattering Methods and Instruments for Medical Diagnosis*, SPIE Press, Tutorial Texts in Optical Engineering, vol. TT38, 2000, pp. 3-11.

Tunér, Jan, et al., *Low Level Laser Therapy, Clinical Practice and Scientific Background*, Prima Books in Sweden AB, 1999, pp. 1-9, 45-58, 59-109, 62-114; 113-116, 118, 132-134, 134-135; 149-151; 151-156; 185; 334-364.

Wong-Riley Margaret T.T., et al., *Light-emitting diode treatment reverses the effect of TTX on cytochrome oxidase in neurons*, NeuroReport, vol. 12, No. 14, Oct. 8, 2001, pp. 3033-3037.

Yaakobi, Tali et al., *Long-term effect of low energy laser irradiation on infarction and reperfusion injury in the rate heart*, J. Appl. Physiol., vol. 90, 2001, pp. 2411-2419.

\* cited by examiner

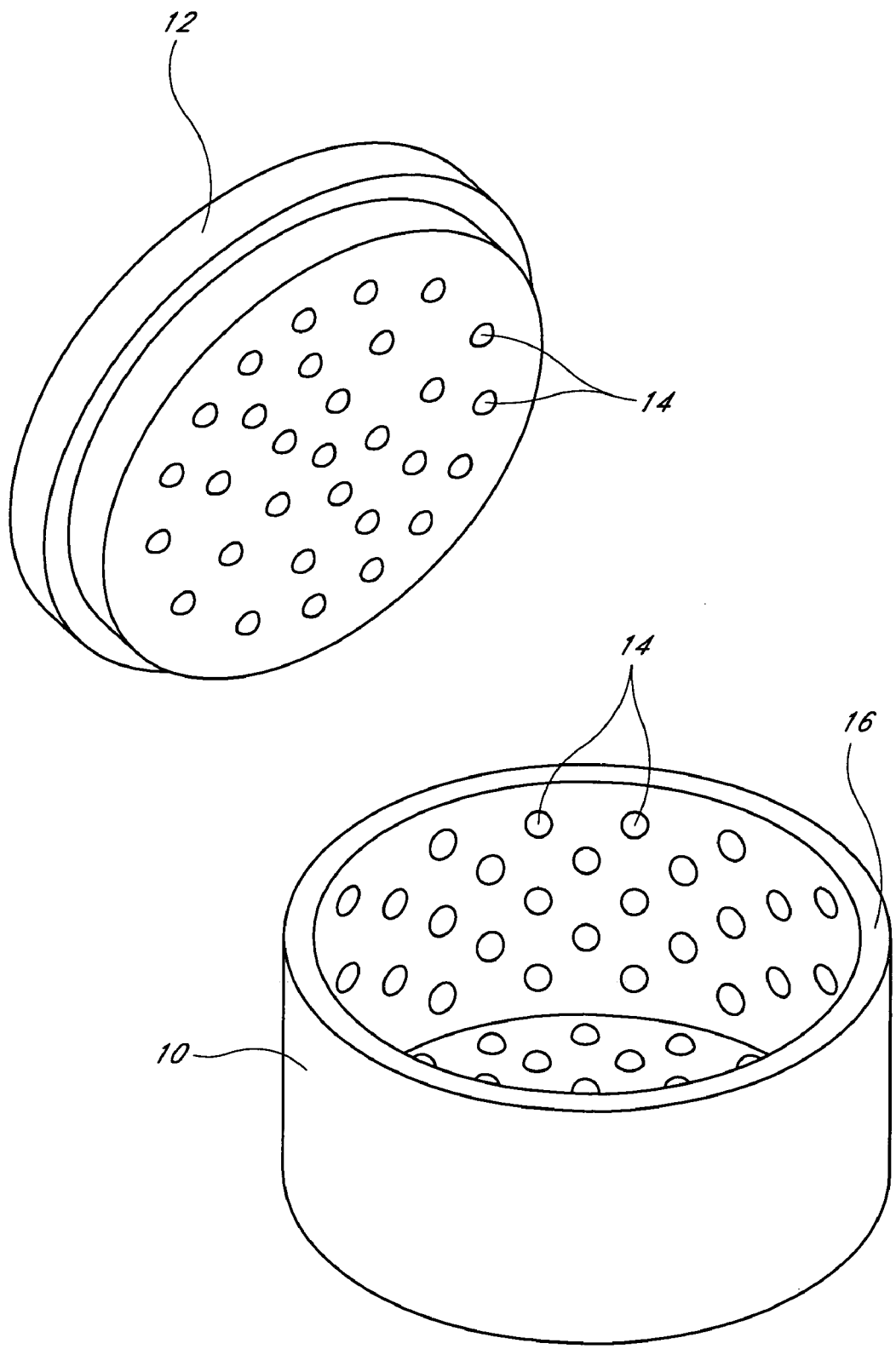

METHOD FOR PRESERVING ORGANS FOR TRANSPLANT

RELATED APPLICATION INFORMATION

This application claims priority under 35 U.S.C. § 119(e) to U.S. Provisional Application Ser. Nos. 60/347,171, filed Jan. 9, 2002, and 60/353,639, filed Jan. 31, 2002, the entireties of which are hereby incorporated by reference.

FIELD OF THE INVENTION

The present invention relates to apparatus and methods for preserving tissue, such as harvested organs for transplant.

BACKGROUND OF THE INVENTION

Over the past thirty years, solid organ transplantation has become an increasingly viable treatment option for a variety of diseases and conditions. For example, in the United States alone, kidney transplants are now performed at an annual rate of over 9,000, and heart transplants are performed at the rate of over 1,500 per year. However, rejection of the transplanted tissue due to the recipient's normal immune response and transplant-related pathophysiology in the graft tissue continues to be a major hurdle to successful transplantation. In particular, graft tissue quality is a major factor underlying graft rejection. The method of storing a donor organ once removed from the donor greatly impacts.

Typically, once a donor organ is harvested, the organ is preserved by storage in a portable hypothermic container under sterile conditions. Thus, methods to preserve donor tissue integrity have focused primarily on maintenance of properly hypothermic and sterile conditions. However, tissue integrity compromised after harvesting and during storage remains a barrier to improved long-term survival of organ transplants. Even under carefully monitored hypothermic and sterile conditions, ischemia and reperfusion injury negatively impact donor tissue quality. In particular, ischemic damage to the vascular endothelium can result in accelerated graft atherosclerosis, which adversely affects ultimate survival of the graft. In addition, compromised donor tissue contributes to other chronic pathologies in the graft that result in substantial rates of graft loss.

The problem of compromised organ tissue integrity is a major factor contributing to inadequate supplies of organs for transplant. About one in four patients awaiting cardiac transplantation dies while waiting for a suitable donated heart, and similar supply problems plague candidate recipients of other organs. The waits are due in part to insufficient rates of organ donation from potential donors, but also due in part to insufficient progress in developing successful techniques for preserving donated organs beyond very limited time periods after harvesting. Recent advances in immunosuppressive therapy that otherwise after harvesting. Recent advances in immunosuppressive therapy that otherwise have made organ transplantation more feasible have merely exacerbated the problems of organ supply. Thus, a major hurdle in exploiting improved organ transplantation techniques has been the inability to extend safe preservation of donated organs beyond the currently accepted time limit of about four hours. Preservation time limits of a few hours effectively limit the geographic area within which a donated organ can be transported and still be successfully transplanted. Such time limits also make it difficult or impossible to meaningfully evaluate the donated organ before transplant.

Known organ preservation approaches typically include hypothermic arrest and storage in a liquid medium or perfusate, such as known cardioplegic preservation solutions for hypothermic preservation of donated hearts. However, such approaches still do not prevent myocardial damage due to ischemia, reperfusion, fluid and electrolyte imbalances leading to edema, and metabolic exhaustion at the cellular level leading to a degradation of high-energy phosphates, all known to be factors contributing substantially to tissue damage.

To avoid the problems associated with hypothermic arrest and storage, it is known in the art that normothermic preservation eliminates the need to arrest organ function and the need for hypothermic storage, and reduces reperfusion injury and other time dependent tissue injury associated especially with metabolic rundown and depletion of high-energy phosphates. Thus, known methods for extending organ preservation involve attempts to simulate near-normal physiologic conditions, using various approaches. One approach involves harvesting almost all the donor's organs and using the system to perfuse the needed organ under normothermic conditions. However, as an element of routine transplant practice, this approach is limited because of the myriad practical difficulties involved in removing and preserving heart, lungs, liver, pancreas, and kidneys all together and all in functioning condition. Another related approach to achieving extended extracorporeal preservation of a donor organ involves providing continuous sanguineous perfusion, while maintaining the donor organ in the normal functioning state. Thus, known approaches include apparatus, methods and physiologic media that create an extracorporeal circuit for sanguineously perfusing the harvested organ at normothermic temperatures, thus prolonging preservation of the harvested organ for up to about twenty-four hours or longer. However, such approaches remain relatively cumbersome, are relatively costly, are not readily amenable to transport because they involve fairly complex perfusion systems, and have met with limited success.

In the field of surgery, high-energy laser radiation is now well accepted as a surgical tool for cutting, cauterizing, and ablating biological tissue. High-energy lasers are now routinely used for vaporizing superficial skin lesions and, and to make deep cuts. For a laser to be suitable for use as a surgical laser, it must provide light energy at a power sufficient to heat tissue to temperatures over 50 C. Power outputs for surgical lasers vary from 1-5 W for vaporizing superficial tissue, to about 100 W for deep cutting.

In contrast, low level laser therapy involves therapeutic administration of laser energy to a patient at vastly lower power outputs than those used in high energy laser applications, resulting in desirable biostimulatory effects while leaving tissue undamaged. For example, in rat models of myocardial infarction and ischemia-reperfusion injury, low energy laser irradiation reduces infarct size and left ventricular dilation, and enhances angiogenesis in the myocardium. (Yaakobi et al., *J. Appl. Physiol.* 90, 2411-19 (2001)). Low level laser therapy has been described for treating pain, including headache and muscle pain, and inflammation. The use of low level laser therapy to accelerate bone remodeling and healing of fractures has also been described. (See, e.g., J. Tuner and L. Hode, Low LEVEL LASER THERAPY, Stockholm:Prima Books, 113-16, 1999, which is herein incorporated by reference).

However, known low level laser therapy methods are circumscribed by setting only certain selected parameters within specified limits. For example, known methods are characterized by application of laser energy at a set wavelength using a laser source having a set power output. Specifically, known methods are generally typified by selecting a wavelength of the power source, setting the power output of the laser source at very low levels of 5 mW to 100 mW, setting low dosages of at most about 1-10 Joule/cm$^2$, and setting time periods of application of the laser energy at twenty seconds to minutes. However, other parameters can be varied in the use of low level laser therapy. In particular, known low level laser therapy methods have not addressed the multiple other factors that may contribute to the efficacy of low level laser therapy.

Against this background, a high level of interest remains in finding new and improved methods for preserving harvested organs for transplant thus to extend the time period for preservation. A need thus remains for simple, portable and cost-effective apparatus and methods that provide the ability to extend the organ preservation period beyond accepted limits, while avoiding time-dependent tissue damage due to ischemia and reperfusion, and depletion of high-energy phosphates. A need also remains for apparatus and methods that help to overcome organ transplant rejection, and enhance the survival time of transplanted organs, by improving the tissue quality of transplanted organs.

SUMMARY OF THE INVENTION

The light therapy apparatus and methods for preserving tissue, including organs, for transplant are based in part on the new and surprising discovery that applying electromagnetic energy to the tissue during transport, generally following explantation, appears to prevent or retard tissue damage in a harvested organ, thus extending the time period of preservation and helping to overcome transplant rejection by improving tissue quality in preserved organs. Preferably the electromagnetic energy that is applied falls within a select wavelength range and at a select range of power density (i.e., power per unit area)

In accordance with one embodiment, there is provided an apparatus for transporting living tissue, such as an organ, comprising a tissue preserving container having an interior cooling chamber adapted to receive a tissue, and at least one light source mounted on the container so as to illuminate the interior cooling chamber from a multiplicity of directions, where said light source emits optical radiation which produces a biostimulative effect on a tissue, thereby preventing or retarding damage to said tissue during transport.

Thus, one preferred method relates to preserving organs for transplant and includes delivering to a harvested organ an effective amount of electromagnetic energy, the electromagnetic energy having a wavelength in the visible to near-infrared wavelength range, wherein delivering the effective amount of electromagnetic energy comprises selecting a predetermined power density of electromagnetic energy. The electromagnetic energy is applied to harvested organs placed in a preservation medium or perfusate, and may be applied in a hypothermic environment, for example in a hypothermic container or chamber, or in a normothermic environment. In a preferred embodiment, the power density is selected to be about 0.01 mW/cm$^2$ to about 100 mW/cm$^2$. To deliver the predetermined power density of electromagnetic energy to the organ, such method may further include selecting a power and dosage of the electromagnetic energy sufficient to deliver the predetermined power density of electromagnetic energy to the organ. The electromagnetic energy is then applied to multiple treatment points across the organ surface.

The methods are particularly suitable for preserving solid organs for transplant such as heart, lung, kidney, liver, or pancreas, but may also be used to preserve other tissues or organs.

The methods are further directed toward preventing or retarding rejection of a transplanted organ in a subject in need thereof, the method including delivering to a harvested organ before transplant into the subject an effective amount of electromagnetic energy wherein delivering the effective amount of electromagnetic energy comprises selecting a power density of the electromagnetic energy, preferably about 0.01 mW/cm$^2$ and less than about 100 mW/cm$^2$.

In one embodiment, an apparatus for preserving tissue, such as a harvested organ for transplant includes a media storage container and a primary cover which mates with the media storage container to form a fluid-tight seal. The media storage container has a base and side walls extending from the base, and the side walls have a plurality of openings therethrough, each opening configured to mate with an electromagnetic energy source, such as a laser energy source, to form a fluid tight seal. The media storage container is configured to suspend the harvested organ in a fluid preservation medium. The media storage container is suspended in a secondary container having a base and side walls extending therefrom, the secondary container configured to suspend the media storage container in a thermoregulatory fluid. A plurality of electromagnetic energy sources extend from the side walls, each electromagnetic energy source mating with one of the plurality of openings on the media storage container side walls to form a fluid tight seal against the thermoregulatory fluid. A secondary cover mates with the secondary container. The electromagnetic energy sources are configured to emit electromagnetic energy having a wavelength in the visible to near-infrared wavelength range at a power density selected from the range of about 1 mW/cm$^2$ to about 100 mW/cm$^2$. The apparatus is used to apply electromagnetic energy at a selected power density to a harvested organ suspended in a preservation medium in the media storage container.

BRIEF DESCRIPTION OF THE DRAWINGS

The FIGURE is a perspective view of one embodiment of an apparatus for transporting tissue, such as an organ.

DETAILED DESCRIPTION OF THE PREFERRED EMBODIMENT

The methods to preserve organs for transplant described herein may be practiced and described using, for example, a low level laser therapy apparatus such as that shown and described in U.S. Pat. No. 6,214,035, U.S. Pat. No. 6,267,780, U.S. Pat. No. 6,273,905 and U.S. Pat. No. 6,290,714, which are all herein incorporated by reference together with the references contained therein. In a preferred embodiment, they are practiced using an apparatus such as that shown in the FIGURE.

In accordance with one embodiment of method to preserve organs for transplant is a low level laser apparatus including a handheld probe for delivering the electromagnetic energy to the organ. The probe includes a laser energy source emitting electromagnetic energy having a wavelength in the visible to near-infrared wavelength range, i.e., from about 630 nm to about 904 nm. The probe includes, for example, a single laser diode that provides about 100 mW to about 500 mW of total power output, or multiple laser diodes that together are capable of providing at least about 100 mW to about 500 mW of total power output. Other embodiments provide lower total power output, for example, about 1 mW or about 25 mW. The actual power output is preferably variable using a control unit electronically coupled to the probe, so that power of the light energy emitted can be adjusted in accordance with power density calculations as described below. The diodes used are, for example, continuously emitting GaAIAs laser diodes having a wavelength of about 830 nm. In one embodiment of portable apparatus for tissue transport as described infra, a plurality of such laser probes provide the light energy sources. Alternatively, the electromagnetic energy source is another type of source, for example a light-emitting diode (LED), or other light energy source, having a wavelength in the visible to near-infrared wavelength range. The level of coherence of a light energy source is not critical. A light energy source need not provide light having the same level of coherence as the light provided by a laser energy source.

In preferred methods, the electromagnetic energy has a wavelength in the visible to near-infrared wavelength range, and within a select range of power density (i.e., light intensity or power per unit area, in $mW/cm^2$). The use of power densities within a particular range, as noted herein, appears to be a factor in producing beneficial effects for tissues, such as a harvested organ, thus enhancing preservation of the organ or tissue for transplant. In a preferred embodiment, the electromagnetic energy delivered to an organ or tissue has a power density of about 0.01 $mW/cm^2$ to about 100 $mW/cm^2$, and, independent of the power of the electromagnetic energy source used and the dosage of the energy used, appears to improve the tissue quality of the stored organ, and appears to enhance the preservation period of organs for transplant. In an exemplary embodiment, the electromagnetic energy is applied to an organ stored hypothermically, i.e., under hypothermic arrest, or at least at a temperature below the normal body temperature of the organ. Alternatively, the electromagnetic energy is applied to an organ stored under normothermic conditions, i.e., at near-normal physiologic temperature and function. Under normothermic conditions, it is preferred that the electromagnetic energy is applied to an organ for which a perfusion system and gas-exchange system are supplied, such as that described in U.S. Pat. No. 6,046,046, which is herein incorporated by reference.

In preferred embodiments, the treatment parameters include one or more of the following and the preferred storage and transport apparatus have light sources capable of supplying energy having one or more of the following properties. Preferred power densities of light at the level of the target cells of the tissue are between about 0.01 $mW/cm^2$ and about 100 $mW/cm^2$, including about 0.05, 0.1, 0.5, 1, 5, 10, 15, 20, 30, 40, 50, 60, 70, 80, and 90 $mW/cm^2$. In other embodiments, power densities above 100 $mW/cm^2$, including about 250 $mW/cm^2$ and about 1000 $mW/cm^2$. In embodiments in which something surrounds the tissue or organ during treatment, such as when the organ is kept in contact with a medium such as a preservation medium or perfusate during storage and/or transport, or where it is placed in a bag or the like, one should take into account any possible attenuation of the energy as it travels through such surrounding material. In most embodiments, however, the power density emitted by the source(s) will be substantially identical to the power density at the outside surface of the tissue or organ. To achieve such power densities, preferred light energy sources, each alone or in combination, are capable of emitting light energy having a total power output of at least about 1 mW to about 500 mW, including about 5, 10, 15, 20, 30, 50, 75, 100, 150, 200, 250, 300, and 400 mW, but may also be as high as about 1000 mW or below 1 mW, such as 0.01 mW. Preferably the light energy used for treatment has a wavelength in the visible to near-infrared wavelength range, i.e., from about 630 to about 904 nm, preferably about 780 nm to about 840 nm, including about 790, 800, 810, 820, and 830 nm. The light may contain a large number of wavelengths within this range, or it may be substantially monochromatic (i.e. one wavelength or a very narrow band of wavelengths).

In a preferred embodiment, the treatment proceeds continuously during substantially the entire period of time that the organ or tissue is being stored or transported, for example, during the time between explantation of the tissue or organ from a donor to implantation of the tissue or organ into a recipient, which may be anywhere from a few minutes to several hours. During the treatment, the light energy may be continuously provided, or it may be pulsed. If the light is pulsed, the pulses are preferably at least about 10 ns long, including about 100 ns, 1 ms, 10 ms, and 100 ms, and occur at a frequency of up to about 1 kHz, including about 1 Hz, 10 Hz, 50 Hz, 100 Hz, 250 Hz, 500 Hz, and 750 Hz.

Without being bound by theory, it is believed that generally independently of the power and dosage of the electromagnetic energy used, electromagnetic energy delivered within a specified range of power densities provides a biostimulative effect on mitochondria to avoid degradation of high-energy phosphates that is known to contribute to tissue damage. The electromagnetic energy may also help to avoid other degradation mechanisms and/or enhance protective mechanisms or reactions in the tissue. In any case, the observed biostimulative effect helps to maintain cellular integrity and prevents or retards tissue damage during compromise of the organ's normal physiologic environment, i.e., during disruption of normal perfusion and function such as may occur during hypothermic or normothermic storage before transplant.

The term "organ" as used herein refers to a structure of bodily tissue in mammal such as a human being wherein the tissue structure as a whole is specialized to perform a particular body function. Organs that are transplanted within the meaning of the present methods include skin, cornea, heart, lung, kidney, liver and pancreas. Solid organs include the heart, lung, kidney, liver and pancreas.

The term "transplant" as used herein refers to any organ or body tissue that has been transferred from its site of origin to a recipient site. Specifically in an allograft transplant procedure, the site of origin of the transplant is in a donor individual and the recipient site is in another, recipient individual.

The term "rejection" as used herein refers to the process or processes by which the immune response of an organ transplant recipient mounts a reaction against the transplanted organ sufficient to impair or destroy normal function of the organ. The immune system response can involve specific (antibody and T cell-dependent) or non-specific (phagocytic, complement-dependent, etc.) mechanisms, or both.

The term "effective" as used herein refers to a characteristic of an amount of electromagnetic energy wherein the amount of electromagnetic energy achieves the goal of preventing, avoiding or retarding tissue damage in tissue, such as a harvested organ, whether the tissue damage results from ischemia, reperfusion, degradation of high-energy phosphates, inflammatory responses, edema, or any other tissue response to a stimulus such as the disruption of function and the manipulation that attends harvesting and storage of the organ.

Thus, in a broad aspect, one preferred method is directed toward preserving a harvested organ for transplant include delivering to the harvested organ an effective amount of electromagnetic energy, the electromagnetic energy having a wavelength in the visible to near-infrared wavelength range, wherein delivering the effective amount of electromagnetic energy comprises delivering a predetermined power density of the electromagnetic energy to the organ. In a preferred embodiment, delivering the predetermined power density of electromagnetic energy to the harvested organ involves selecting the predetermined power density to be delivered, selecting a power and dosage of the electromagnetic energy sufficient to deliver the predetermined power density of electromagnetic energy to the organ, and applying the electromagnetic energy to at least one treatment point on a surface of the organ. To deliver the predetermined power density of electromagnetic energy to the organ, the type and size of the organ being treated may be considered, and an appropriate dosage and power of the electromagnetic energy selected. The appropriate dosage and power of energy are any combination of power and dosage sufficient to deliver the predetermined power density of electromagnetic energy to the organ. In addition, the dosage and power should be sufficient for the electromagnetic energy to penetrate any body tissue such as connective tissue or fat that may be interposed between the surface of the organ and the electromagnetic energy source or any preservation medium or other material that may come between the tissue and the light source(s). Further, the selected dosage and power of the electromagnetic energy should be sufficient to traverse any distance interposed between the electromagnetic energy source and the surface of the organ.

The methods and apparatus are especially suitable for preserving for transplant any solid organ, such as a heart, a lung, a kidney, a liver, or a pancreas. However, other tissues and other organs such as skin and cornea may also be beneficially treated using the methods and apparatus.

It is understood that the specific power density selected for treating any specific harvested organ will be dependent upon a variety of factors including especially the type (i.e., heart, liver, etc.) and size of the organ, the wavelength of the electromagnetic energy selected, whether the electromagnetic energy is being applied to an organ under hypothermic; arrest or under normothermic conditions, and the expected preservation time. Thus, the particular power density and other treatment parameters can be chosen to tailor the treatment to the individual organ transplant situation as is understood and determinable by one of skill in the art.

To deliver the selected power density of electromagnetic energy to the interior of a harvested organ, a relatively greater surface power density of the electromagnetic energy is calculated taking into account any attenuation of the energy as it travels from the energy source to a treatment point on the surface of the organ, and through the organ tissue itself. For example, to deliver a predetermined power density of electromagnetic energy deeply within a relatively more massive organ such as a liver will require a greater surface power density than to deliver the same predetermined power density to a relatively less massive organ such as a pancreas. Factors known to affect penetration and to be taken into account in the calculation of the required surface power density include pigmentation and blood content, tissue type (myocardial, renal, etc.), and overall organ size and depth of internal tissue relative to surface treatment points. For example, to obtain a desired power density of about 10 mW/cm$^2$ at a site within an organ at a depth of 3 cm below the organ surface may require a surface power density of 400 mW/cm$^2$. In particular, the higher the level of pigmentation, the higher the required surface power density to deliver a predetermined power density of electromagnetic energy to a subsurface site being treated More specifically, to preserve an organ for transplant, the electromagnetic energy source, for example a hand-held laser probe, is sterilized and placed in contact with a treatment point on a surface of the harvested organ. Alternatively the electromagnetic energy source is positioned over a treatment point on the organ surface, but held some distance away from the treatment point. A surface power density calculation is made taking into account factors including the wavelength of the electromagnetic energy being used, the power density that has been selected from the power density range of about 1 mW/cm$^2$ to about 100 mW/cm$^2$, the depth of tissue being treated, the extent and type of any intervening body tissue such as fat or connective tissue between the energy source and the organ surface, pigmentation, and the like that affect energy penetration and thus the power density that is actually received at the organ treatment point and any depth therebelow. Power of the energy source being used and the surface area of the treatment point are accordingly adjusted to obtain a surface power density sufficient to deliver the predetermined power density of electromagnetic energy to the organ at a given depth within the tissue. The electromagnetic energy source is then energized and the selected power density of electromagnetic energy delivered to the organ.

In an exemplary embodiment, the electromagnetic energy is applied to at least one treatment point on the organ, the treatment point having a diameter of about 1 cm. Thus, to most completely treat a harvested organ which typically will have a surface area substantially larger than a spot of a diameter of about 1 cm in accordance with this embodiment, the electromagnetic energy is applied sequentially to a series of multiple treatment spots having centers that are separated by at least about 1 cm. The series of treatment spots can be mapped out over the surface of the organ to aid in an orderly progression of electromagnetic energy applications that systematically cover the surface area of the organ as it is being treated from any one approach. Some organs may be susceptible of treatment from more than one approach, i.e., treatment from the frontal and rear aspects of the organ, or from the frontal and side aspects. As the approach is changed, the required surface power density to deliver the predetermined power density of electromagnetic energy to the organ may change: depending on whether and how the depth of the organ tissue being treated relative to the organ surface changes, and any change in the nature and extent of any intervening tissue. Alternatively, the organ may be treated by applying the electromagnetic energy to two or more spots simultaneously, or to the entire organ at once.

Within a preferred power density range, the precise power density selected for treating the organ is determined according to the judgment of a trained healthcare provider or light therapy technician and depends on a number of factors, including the specific wavelength of electromagnetic energy selected, and clinical factors such as type of organ being treated, the current survival time of the organ, the expected preservation time, whether the organ is being preserved under hypothermic arrest or under normothermic conditions, and the like. It should be understood that the power density of electromagnetic energy might be adjusted as preservation time elapses, or for use in combination with any other preservation agent or agents, especially agents added to a preservation medium or perfusate to achieve the desired effect of reducing tissue damage during preservation. For example, as preservation time elapses, it will be expected that the number (i.e., number of treatment points) and/or frequency of electromagnetic energy treatments should increase, and/or the selected power density will increase to achieve the desired effect of reducing tissue damage during preservation. Generally, as long as the harvested organ remains viable, the electromagnetic energy therapy can be applied on a regular basis such every quarter- or half-hour, or hourly, or any other suitable period of time.

In another aspect, there is provided an apparatus for preserving a harvested organ for transplant. In an exemplary embodiment, the apparatus is a "light box," including generally a media storage container for receiving the harvested organ and suspending the organ in a fluid preservation medium or perfusate, and means for applying electromagnetic energy in accordance with the methods described above, i.e., at a selected power density, and wavelength, to the organ therein contained. The basic configuration of one preferred type of "light box" is, for example, described in U.S. Pat. No. 4,951,482, which is herein incorporated by reference.

In an exemplary embodiment, the apparatus is a portable container suitable for hypothermic transport of donor organs, and includes a media storage container having a base and side walls extending from the base. The side walls have a plurality of openings therethrough, each opening configured to mate with an electromagnetic energy source, such as a laser probe as described supra, or LED or other light source, to form a fluid tight seal. The openings are configured, for example, with threads and an O-ring type gasket, the threads configured to mate with threads on an end of a laser probe serving as a laser energy source. The media storage container is configured to allow for suspension of the harvested organ in a fluid preservation medium, and a primary cover mates with the media storage container to form a fluid-tight seal. In this exemplary embodiment, the apparatus further includes a secondary container having a base and side walls extending therefrom, and is configured to suspend the media storage container in a thermoregulatory fluid. A plurality of electromagnetic energy sources, for example laser energy sources, extend from the side walls of the secondary container. In one embodiment, each energy source mates with one of the plurality of openings on the media storage container side walls to form a fluid-tight seal against a thermoregulatory fluid contained in the secondary container. Similarly, the fluid-tight seal of the primary cover with the media storage container seals inside of the media storage container against the thermoregulatory fluid. In accordance with the methods described herein, the energy source(s) are preferably configured to emit light energy having one or more of the characteristics described supra. The energy sources and organ are positioned relative to one another so that the energy sources direct the energy at the organ contained in the media storage container. In one embodiment, a secondary cover mates with the secondary container to contain a thermoregulatory fluid. The media storage container is sized appropriately to receive and secure a large solid organ up to about the size of an adult human liver or lung. The secondary container is sized appropriately to receive the media storage container and a sufficient amount of thermoregulatory fluid to properly maintain the hypothermic arrest of the organ, while yet remaining sufficiently compact that a single individual adult is able to carry or otherwise transport the apparatus. It will be appreciated that the apparatus and methods can be varied for application to organs maintained in a normothermic environment, e.g., in an environment at near-normal physiologic temperature while maintaining near-normal organ function. For example, under normothermic conditions the light energy will be applied to an organ for which a perfusion system and gas-exchange system are supplied, such as that described in U.S. Pat. No. 6,046,046, which is herein incorporated by reference.

One preferred embodiment of tissue or organ transport apparatus is illustrated in the FIGURE. The apparatus includes a container to receive and hold the tissue or organ. The container comprises a bottom portion 10 and a cover 12. The bottom portion 10 may be any suitable shape including, but not limited to, those having a base and at least one wall, such as the generally cylindrical shape illustrated in the FIGURE. The shape of the interior of the bottom portion may or may not correspond to its exterior shape. For example, the bottom portion of an embodiment may have a generally cubic exterior yet have a hemispherical shaped interior. In preferred embodiments, the exterior of the bottom portion 10 has at least one flat surface, preferably opposite the open end which mates with or engages the cover 12, so as to provide a stable resting surface for the apparatus. The cover 12 is shaped so as to mate with the bottom portion. In a preferred embodiment, the cover 12 and bottom portion 10 form a fluid-tight seal when placed together to aid in containment of any storage or preservation medium or bodily fluids that may be associated with the organ or tissue. The cover 12 and bottom portion 10 need not be two separate, removable pieces as illustrated; they may be single piece construction or attached together such as by a hinge or other such mechanism. The cover 12 and bottom portion 10 may further comprise a locking or latching mechanism, engaging threads or other suitable means for securing the two pieces together. A handle may also be included to assist in transporting the apparatus.

The cover 12 and/or the bottom portion 10 have at least one light source 14 mounted thereon to provide the electromagnetic energy to the tissue. In embodiments having more than one source 14, the light sources may be separate or a single electromagnetic energy emitter may be used to provide light to two or more sources 14 simultaneously or in some sequence. In preferred embodiments, the source(s) illuminate the interior from a plurality of directions. In a preferred embodiment, the source(s) 14 is attached to a controller (not illustrated) that is set or programmed to deliver light having characteritics as desired for treatment, including, but not limited to, wavelength, power, pulse duration, pulse frequency, and, in some embodiments, to vary the treatment parameters over time. In one embodiment, the bottom portion 10 further comprises a shelf or elevated portion upon which the organ or tissue is placed to provide spatial separation between the organ or tissue and one or more sources 14.

In preferred embodiments, the interior of at least the bottom portion 10 forms a cooling chamber to allow for storage and transport of the tissue received therein at a lowered temperature, including temperatures sufficient to cause hypothermic arrest. The cooling chamber is cooled by any suitable method or means. In some preferred embodiments, one or more walls 16 of the bottom portion have a cooling means disposed therein, including, but not limited to, electric (or battery) powered cooling equipment (e.g. heat pump, refrigeration, Peltier effect), thermoregulatory fluid, ice, "blue ice", dry ice, and the like.

In another embodiment, the electromagnetic energy therapy methods and apparatus are used to enhance growth and function of organ-derived cell lines used in bioartificial organ support systems such as that described in U.S. Pat. No. 5,368,555 which is herein incorporated by reference. For example, the electromagnetic energy is applied to a hepatic cell line that lines a hollow fiber cartridge. Biostimulation provided to the hepatocytes or other cell line enhances growth and function of the hepatocytes to perform key organ-specific functions in a subject for whom organ function is compromised. Improving the growth and function of such cell lines as used within such bioartificial organ support systems mitigates organ supply problems, especially for patients with acute and substantial loss of organ function.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. An apparatus for transporting living tissue, such as an organ, comprising:
    a tissue preserving container having at least one wall surrounding an interior chamber that receives a tissue, the at least one wall having a plurality of openings therethrough; and
    at least one light source mounted on the container and extending through the openings into the interior chamber so as to illuminate the tissue within the interior chamber from a multiplicity of directions during transport of the apparatus;
    said light source emitting optical radiation which produces a biostimulative effect on the tissue, thereby preventing or retarding damage to said tissue during transport.

2. An apparatus according to claim 1 wherein the light source emits optical radiation having a power density at the tissue of at least about 1 mW/cm$^2$.

3. An apparatus according to claim 1 wherein the light source emits optical radiation having a power density at the tissue of about 2 mW/cm$^2$ to about 20 mW/cm$^2$.

4. An apparatus according to claim 1 wherein the light source emits optical radiation having a wavelength of about 630 nm to about 904 nm.

5. An apparatus according to claim 4, wherein the radiation has a power density at the tissue of about 0.1 mW/cm$^2$ to about 20 mW/cm$^2$.

6. An apparatus according to claim 1 wherein the light source is an LED.

7. An apparatus according to claim 1, wherein the light source emits optical radiation having a wavelength of about 780 nm to about 840 nm.

8. An apparatus according to claim 7, wherein the radiation has a power density at the tissue of about 0.1 mW/cm$^2$ to about 20 mW/cm$^2$.

9. An apparatus according to claim 1, wherein the light source emits energy in pulses.

10. An apparatus according to claim 9, wherein the light pulses occur at a frequency of about 1 Hz to 1 KHz.

11. An apparatus according to claim 1, wherein the transport of the apparatus is for a period of at least four hours.

12. An apparatus according to claim 1, wherein the at least one light source mates with each opening to form a fluid tight seal.

13. An apparatus according to claim 1, further comprising a secondary container having a plurality of walls, the secondary container configured to suspend the interior chamber in a thermoregulatory fluid.

14. An apparatus according to claim 13, wherein the at least one light source extends from the plurality of walls and mates with the openings to form a fluid tight seal against the thermoregulatory fluid.

15. An apparatus for transporting living tissue, such as an organ, comprising:
    a container comprising a hollow chamber that retains tissue and at least one wall surrounding the chamber, the at least one wall having a plurality of openings therethrough; and
    a plurality of light sources extending through the openings and within the chamber so as to illuminate the tissue within the chamber from several directions during transport of the apparatus;
    wherein said light sources emit optical radiation having a wavelength of about 630 nm to about 904 nm which produces a biostimulative effect on tissue, thereby preventing or retarding damage to the tissue within the chamber during transport.

16. An apparatus according to claim 15 wherein the light sources emit optical radiation having a power density at the tissue of about 0.1 mW/cm$^2$ to about 20 mW/cm$^2$.

17. An apparatus according to claim 15, wherein the light sources emit optical radiation having a wavelength of about 780 nm to about 840 nm.

18. An apparatus according to claim 15, wherein the light sources emit energy in pulses.

19. An apparatus according to claim 18, wherein the light pulses occur at a frequency of about 1 Hz to 1 KHz.

20. An apparatus according to claim 15, wherein the transport of the apparatus is for a period of at least four hours.

21. An apparatus according to claim 15, wherein the plurality of light sources mate with the openings to form fluid tight seals.

22. An apparatus according to claim 15, wherein further comprising a secondary container having a plurality of walls, the secondary container configured to suspend the chamber in a thermoregulatory fluid.

23. An apparatus according to claim 22, wherein the plurality of light sources extend from the plurality of walls and mate with the openings to form fluid tight seals against the thermoregulatory fluid.

* * * * *